United States Patent
Ye et al.

(10) Patent No.: US 7,998,081 B2
(45) Date of Patent: Aug. 16, 2011

(54) COMPUTER ASSISTED CARDIOGRAM DIAGNOSTIC SYSTEM AND THE METHOD THEREOF

(75) Inventors: Wenyu Ye, Nanshan (CN); Junbiao Hong, Nanshan (CN); Shufeng Li, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1254 days.

(21) Appl. No.: 11/635,405

(22) Filed: Dec. 5, 2006

(65) Prior Publication Data

US 2008/0015450 A1    Jan. 17, 2008

(30) Foreign Application Priority Data

Jul. 14, 2006    (CN) .......................... 2006 1 0061701

(51) Int. Cl.
*A61B 5/02* (2006.01)
*A61B 5/0452* (2006.01)

(52) U.S. Cl. ........ 600/508; 600/509; 600/513; 600/300; 128/925

(58) Field of Classification Search .................. 600/509, 600/513, 508, 300; 128/925
See application file for complete search history.

(56) References Cited

U.S. PATENT DOCUMENTS

| | | | |
|---|---|---|---|
| 2003/0204146 A1* | 10/2003 | Carlson | 600/515 |
| 2005/0027202 A1 | 2/2005 | Ginzburg et al. | |
| 2005/0228305 A1* | 10/2005 | Nagata et al. | 600/509 |

FOREIGN PATENT DOCUMENTS

| | | |
|---|---|---|
| CN | 1294898 | 5/2001 |
| CN | 1393204 | 1/2003 |

OTHER PUBLICATIONS

Prineas R, Crow R, Blackburn H. The Minnesota Code Manual of Elctrocardiographic Findings. John Wright-PSG, Inc. littleton, MA, Jun. 1982. http://www.sph.umn.edu/epi/ecg/mncode.pdf.*
Feng, Chen et al., "A Conflict Resolution Mechanism for Multi-Agent Cooperative Diagnosis and its Application," Dept. of Electronic Engineering, University of Science and Technology China, vol. 13, No. 4, Dec. 2000, pp. 395-399.
Yanmei Zhang, "ECG Signal Processing and Automatic Diagnosis," Master's Thesis, Southeast University.

* cited by examiner

*Primary Examiner* — Niketa Patel
*Assistant Examiner* — Joseph Stoklosa
(74) *Attorney, Agent, or Firm* — Kory D. Christensen; Stoel Rives LLP (57) ABSTRACT

A computer assisted cardiogram diagnostic system, comprises a diagnosing unit, for obtaining a plurality of preliminary diagnostic results according to the cardiogram signals; and an amending unit, for judging the plurality of preliminary diagnostic results, and amending the plurality of preliminary diagnostic results using conflict eliminating rules, in order to obtain amended diagnostic results.

16 Claims, 9 Drawing Sheets

COMPUTER ASSISTED CARDIOGRAM DIAGNOSTIC SYSTEM AND THE METHOD THEREOF

RELATED APPLICATION DATA

This application claims priority to Chinese Patent Application No. 200610061701.1, filed on Jul. 14, 2006, the entire disclosure of which is expressly incorporated by reference herein.

FIELD

The application relates to the field of cardiogram signal processing, and in particular to a computer assisted cardiogram diagnostic system and the method thereof.

BACKGROUND ART

A computer assisted cardiogram diagnosis is to analyze the cardiogram signal automatically, and to provide commonly used parameters of clinical diagnosis as well as possible diagnostic conclusions for physicians' reference. The study of computer assisted cardiogram diagnosis started from 1960. At the beginning, it was confined to research in laboratories only. However, it has been incorporated into clinical practices gradually. Up to now, some of the programs are even available for commercial distributions. The method of computer assisted cardiogram diagnosis can be sorted into two approaches: the first is to construct parameters using purely engineering analytic method, for recognizing or predicting particular pathological signals, such as the complexity index for judging ventricular fibrillation, the hidden Markov matrix for judging atrial fibrillation, the heart-rate variance analysis index for calculating threat of a sudden death, and etc.; whereas, the second is to simulate the process of a clinical judgment done by a physician, by means of converting and quantifying his/her judging method, for achieving a corresponding diagnostic analyzing function. The first approach is generally used to discriminate for recognizing a minority of particular pathological signals, and it mainly remains in research at present. By comparison, the second approach has seen a wider usage, by which more types of pathological signal diagnoses can be achieved.

In the actual design of a computer assisted diagnostic system, the judging method applied in the system is unlikely to be made perfect in a single time of design. Usually, a prototype is designed in the first place, whereof the method is modified over and over again through a large number of clinical tests. If it was a regular logic judging structure adopted, each of the modifications will surely cause tremendous changes to the rules for the judgment. Currently, direct logical judgment in simulation of a physician's judgment process is commonly used to achieve those corresponding functions. However, when there are hundreds of types of pathology to be judged, the rules for the pathological judgment may conflict or overlap with each other, thereby making the logical structure of the program extremely complicated and the process of judgment vulnerable to mistakes. To solve the conflicts between those diagnostic rules, therefore, it requires that the logical structure of the direct judgment process be adjusted and modified, and if to adjust the logical structure, the existing system must be largely updated and modified, as a result of which the improvement and maintenance of the diagnostic systems will be rendered extremely difficult.

As an infrequent approach, expert inference system software is also used to provide the judgment by registering those relating rules into the system and depending on the kernel of the expert inference system for executing the judgment. For example, the ECG Criteria Language (ECL), as one of commercial expert inference systems, defines a co-understandable language between the physician and the computer. In that system, the diagnostic analysis is completed via the inferring kernel as the diagnostic rules of the physicians are registered into the system. However, since the approach cannot be separated from the deriving kernel, its applications in practice are strictly limited.

SUMMARY

An object of the present application is to solve the above-mentioned problems, and thus to provide a computer assisted cardiogram diagnostic system and a method thereof, whereby an computer assisted diagnostic analysis can be performed on cardiogram signals based on a simulation of physicians' diagnosis process and a library of diagnostic rules constructed out of the clinical experience of the physicians. Due to simplified process for recognizing and judging large numbers of pathological signals, in particular, the overall inferring process is rendered brief and clear, while the whole diagnostic system is made easy to maintain, update and improve.

In order to achieve the above object, the present application describes a computer assisted cardiogram diagnostic system, comprising: a symbol set, for storing symbols abstracted from the parameters used in cardiogram diagnosis; a characteristic parameter calculating and symbolizing means, for receiving the cardiogram signals, calculating characteristic parameters of the cardiogram signals, and determining symbol values of the characteristic parameters according to the symbols defined for the cardiogram diagnostic parameters as stored in the symbol set; a diagnostic rule library, for storing various rules for diagnoses of the pathological signals relating to cardiogram, and converting each diagnostic rule into a symbol-based rule according to the symbols in the symbol set; an inferring means, for inferring and judging the symbol values of the characteristic parameters based on the diagnostic rules stored in the diagnostic rules library, and determining a preliminary diagnostic result; a conflict-eliminating rule library, for storing the discriminating relations between easily confusable diagnoses types and the priority levels thereof; and a conflict eliminating means, for discriminating and analyzing the types of the preliminary diagnostic results based on the conflict eliminating rule library so as to optimize the preliminary diagnostic results.

Moreover, each diagnostic rule in the diagnostic rule library is assigned with a corresponding characteristic identifying ID, and the preliminary diagnostic result determined according to this diagnostic rule is assigned with the same characteristic identifying ID.

The conflict eliminating rule library adopts a binary tree structure to define the elimination relations between the diagnostic types to be discriminated. Each node therein comprises a type ID of the node, pointers to a left and a right node respectively and a discrimination function, said discrimination function is used for discriminating between the node and its parental node.

Moreover, the conflict eliminating means preferably comprises: a reading unit, for reading a characteristic identifying ID in the preliminary diagnostic result list sequentially, and treating the read characteristic identifying ID as a currently to-be-discriminated ID; a searching unit, for searching in the conflict eliminating rule library a node with the type ID that is identical with the currently to-be-discriminated ID, wherein the search is conducted by taking left child node in the first place, and a control signal is output to the reading unit when the node is not found, while a control signal is output to a first recursive invoking unit when the node is found. It should be noted that the search can be also conducted by taking right child node in the first place; a first recursive invoking unit, for receiving the control signal output by the searching unit, and recursively invoking a conflict eliminating module; the conflict eliminating module comprising: a first determining unit, for determining whether the type ID of a current node is included in the preliminary diagnostic result, wherein a control signal is output to a second determining unit when the determination is positive, and a control signal is output to a third unit determining unit when the determination is negative; a second unit determining unit, for determining whether the current node has a left child node in response to the control signal output by the first determining unit, wherein a control signal is output to a second recursive invoking unit when the determination is positive, and a control signal is output to a discriminating unit when the determination is negative; a second recursive invoking unit, for recursively invoking the conflict eliminating module; a discriminating unit, for making a discrimination by invoking the discrimination function of the current node, and deleting the type that should be removed from the preliminary diagnostic result list based on the result of the discrimination; and a third unit determining unit, for determining whether the current node has a right child node, which outputs a control signal to the second recursive invoking unit when the determination is positive.

Moreover, the system also comprises a memory for storing intermediate inference results.

A computer assisted cardiogram diagnostic method is also configured to achieve above mentioned object, which comprises the following steps:

A1: receiving cardiogram signals and calculating the characteristic parameters thereof.

B1: determining the symbol values of characteristic parameters according to the symbol values, which are defined for those cardiogram diagnosis parameters, in the symbol set.

C1: inferring and judging the diagnostic rules in the symbolized diagnostic rule library based on the symbol values of the characteristic parameters, and determining a preliminary diagnostic result.

D1: discriminating and analyzing the preliminary diagnostic result for an optimization thereof based on the content of the conflict eliminating rule library which defines the discriminating relations and priority levels of the types that may be easily confused.

Moreover, each diagnostic rule in step C1 is assigned with a corresponding characteristic identifying ID, the preliminary diagnosis result determined by the diagnostic rule is assigned with an identical characteristic identifying ID.

The conflict eliminating rule library in step D1 adopts a binary tree structure to define the elimination relations between diagnostic types to be discriminated, wherein, each node comprises a type ID of the node, pointers of a left and a right child node respectively and a discrimination function. The discrimination function is used for discriminating between the node and its parental node.

Moreover, the step D1 preferably comprises the following steps:

D11: reading a characteristic identifying ID in the preliminary diagnostic result list, and treating it as a currently to-be-discriminated ID.

D12: searching a node with the type ID that is identical with the currently to-be-discriminated ID in the conflict eliminating rule library, wherein, the search is conducted by taking left child node in the first place, and proceeding to step D13 when the node is found, otherwise, proceeding to D14.

D13: taking the node as the current node, and invoking conflict eliminating procedure.

D14: reading the next characteristic identifying ID in the preliminary diagnosis result list as the currently to-be-discriminated ID.

The conflict eliminating procedure comprises the following steps:

D131: determining whether the preliminary diagnostic result includes an ID matched with the currently to-be-discriminated ID: if the determination is positive, going to step D132, otherwise, going to step D135.

D132: determining whether the current node has a left child node: if the determination is positive, going to step D133, otherwise, going to step D134.

D133: treating the left child node as a current node, and invoking a conflict eliminating procedure recursively.

D134: invoking the discrimination function of the current node and making discrimination therewith, wherein a type deserving removal is deleted from the preliminary diagnostic result list according to the discrimination result.

D135: determining whether the current node has a right child node: if the determination is positive, going to step D136, otherwise, the procedure is over;

D136: treating the right child node as the current node, and invoking conflict eliminating procedure recursively.

A further improvement featuring is that, the step C1 further comprises steps as follows. Intermediate inference results are stored into a memory. If an inference process involves reference to the other rules, then the memory is searched in first for checking whether the rule has been determined before. If the rule has already been determined, then the rule is enabled for direct reference, otherwise, the current inference process is saved and the system turns to inference of the rule being referred to. The original inference process will be restored when the inference of the reference rule is over.

The features and advantages of the embodiments will be explained in detail in conjunction with the accompanied drawings.

DETAILED DESCRIPTION

Figure 1:
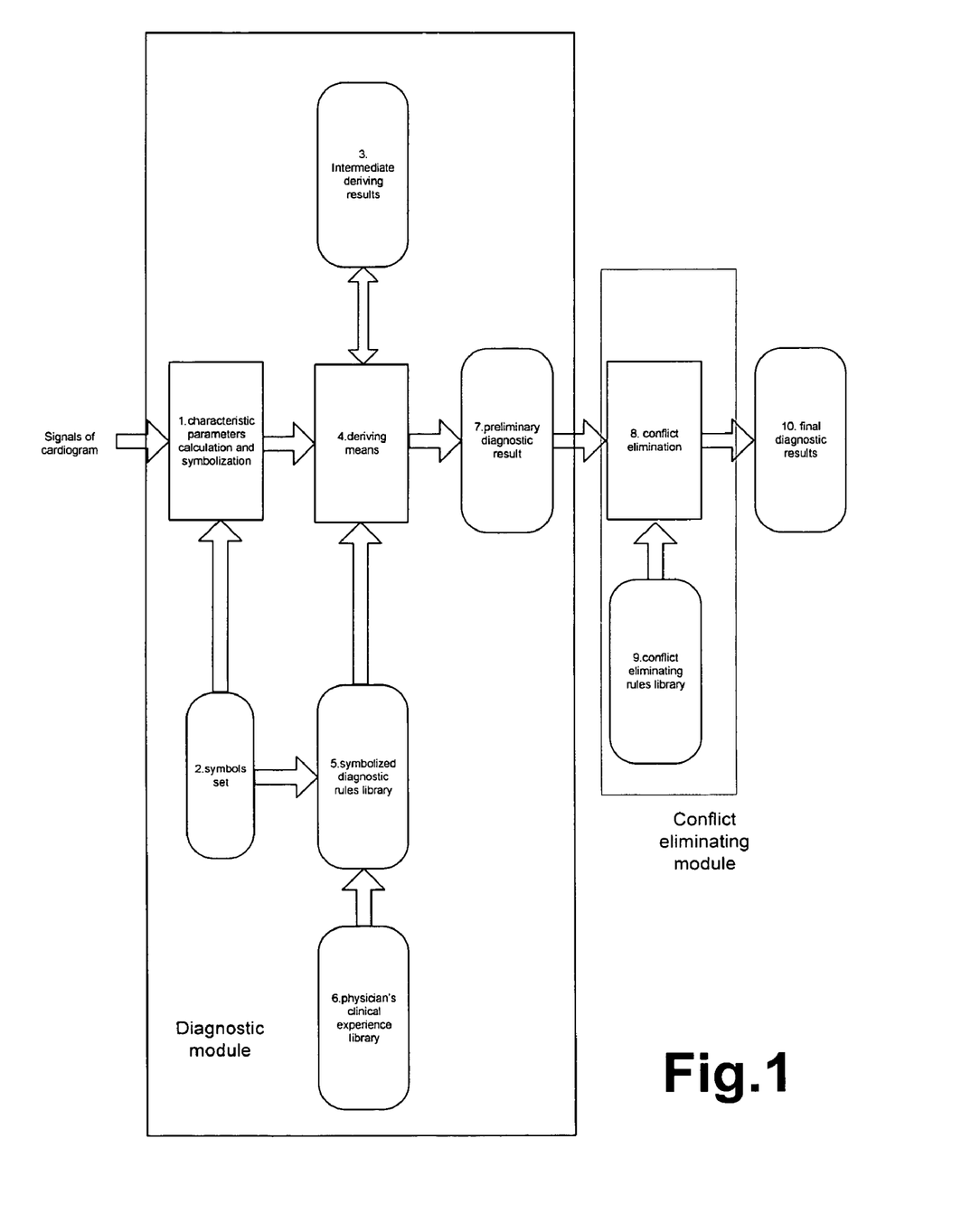
FIG. 1 is a circuit connection block diagram according to one embodiment.

As shown in FIG. 1, a computer assisted cardiogram diagnostic system of the embodiment comprises: a characteristic parameter calculating and symbolizing device 1, a symbol set 2, an intermediate inference result memory 3, a inference machine 4, a symbolized diagnostic rule library 5, a physician diagnostic rule library 6, a preliminary diagnostic result storing device 7, a conflict eliminating device 8, a conflict eliminating rule library 9, and a final result outputting device 10. Therein, the characteristic parameter calculating and symbolizing device 1, the symbol set 2, the intermediate inference result memory 3, the inference machine 4, the symbolized diagnostic rule library 5, the physician diagnostic rule library 6 and the preliminary diagnostic result storing device 7 together constitute a diagnostic module, and the conflict eliminating device 8 and conflict eliminating rule library 9 together constitute a conflict eliminating module.

The symbol set 2 is used to store symbols abstracted from the cardiogram parameters, which is generalized from the physician diagnostic rule library 6. The descriptions in the physician diagnostic rule library are abstracted into a small number of symbols so that the whole physician diagnostic rule library can be expressed as several uniform symbols. The symbol set is just a collection of such abstracted symbols which include symbols converted from the parameters commonly used in conventional diagnoses, such as heart rate, PR period, width of P wave, width of QRS, magnitude of each waveform, and also symbols converted from the terminologies commonly used by the physicians, such as Delta wave, bifid P wave, prominent P wave, and flattened T wave etc.

Figure 2:
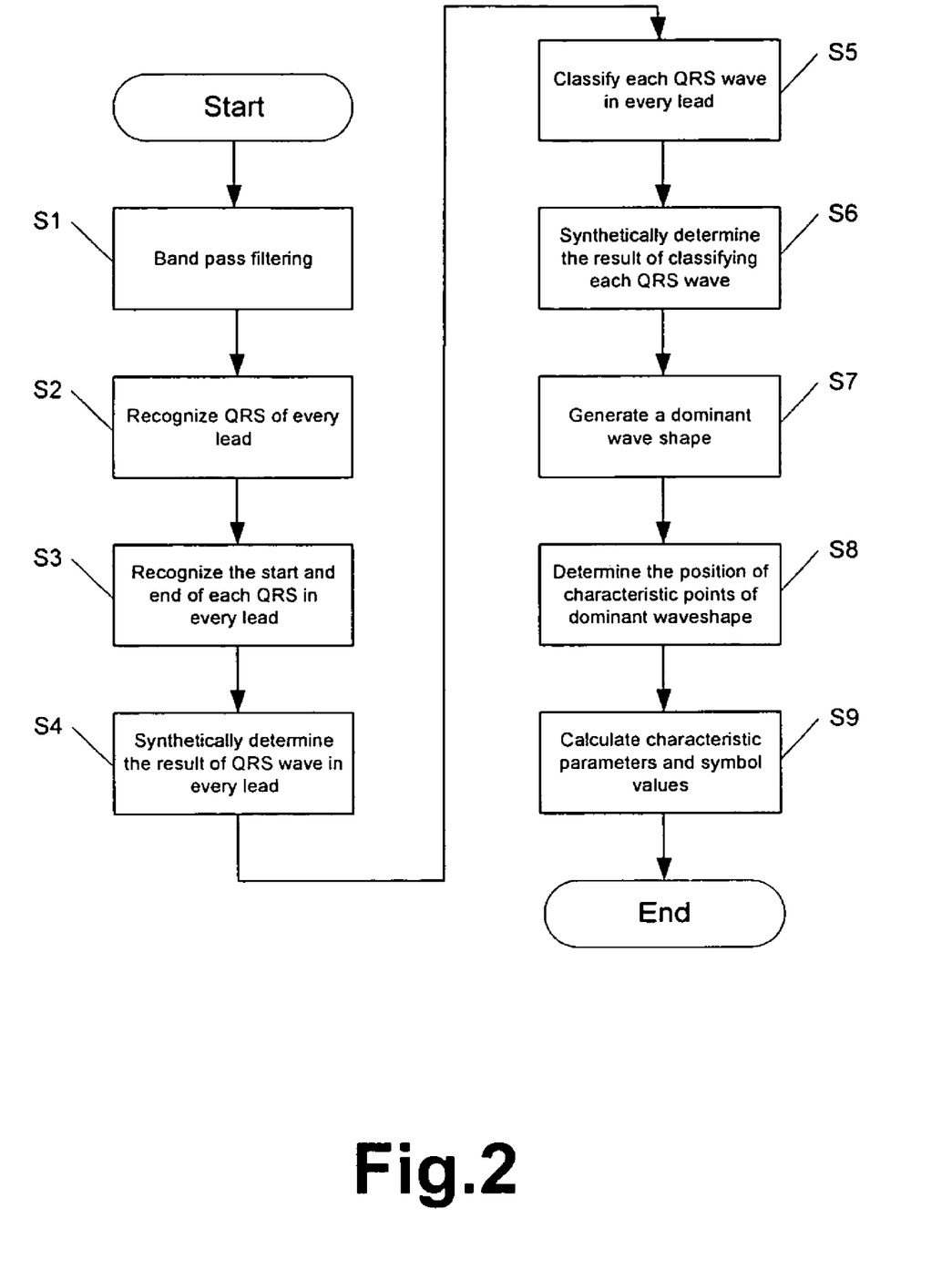
FIG. 2 is a flowchart showing the calculation of characteristic parameters according to one embodiment.

The characteristic parameter calculating and symbolizing device 1 receives the cardiogram signals, pre-processes the signals, suppresses the interfering signals, classifies each heartbeat, extracts the representative wave shapes therein for analysis, calculates the characteristic parameters of the cardiogram signals, and determines the symbol values of the characteristic parameters according to the symbol values defined for the cardiogram diagnostic parameters. A detailed flow thereof is shown in FIG. 2, which includes the following steps:

In step S1, the device 1 suppresses the possible noise interference by band-pass filtering the signals of each channel.

In step S2, it locates the QRS by determining the slope of the processed signals.

In step S3, it preliminarily identifies the start and end points of each QRS wave by analyzing the slope.

In step S4, it corrects the discrimination result of each lead QRS wave, thereby obtaining the final discrimination result of QRS wave as well as result of start and end points of QRS.

In step S5, it classifies QRS wave of each channel into normal wave, supra-ventricular premature beat and ventricular premature beat by analyzing the change of QRS period, the width of QRS and relating coefficients between each QRS wave.

In step S6, it finishes a final determination of each lead QRS wave position and type by synthesizing all results of the lead analysis.

In step S7, it selects, if normal waves exist, three normal waves (at most) with higher relating coefficients for an averaging process, and obtains a dominant wave therefrom; whereas if there are no normal waves present, it proceeds to a subsequent rhythm analysis.

In step S8, it identifies the characteristic start, end points and characteristic waveform of every detailed waveform with respect to the dominant waveform, wherein, the characteristic start and end points include start and end points of P wave, start and end points of QRS wave, as well as start and end points of T wave.

In step S9, it determines the pre-defined symbol values based on the analysis results, wherein some of the symbol values can be obtained from the analysis results directly, such as heart rate, PR period, width of P-wave, width of QRS, magnitude of each wavelength, and etc.; whereas some of the symbol values should be obtained from a further analysis on specified data of the signals, such as whether there is a Delta wave, type of the P wave shape, type of the QRS wave shape, type of the ST wave shape and whether there is pause in QRS wave etc.

The diagnostic rule library 5 is constructed based on the physician diagnostic rule library 6. The physician diagnostic rule library 6 comprises judging criteria for all the pathological signals, which is based on the clinical experience of the physicians and relating literatures. The expressions of the judging criteria are similar to those of a natural language, which employ uniform concepts and explicit quantification relations to the best. The concepts in the library are converted into specific symbols in order to form symbol set 2. Diagnostic rule library 5 stores diagnostic rules relating to various pathological signals of cardiogram. These diagnostic rules are symbolized rules that are converted from each respective diagnostic rules based on the symbol values defined for the cardiogram diagnosis parameters in the symbol set 2. Each diagnostic rule is assigned with a corresponding characteristic identifying ID, and the preliminary diagnostic result determined in accordance with the diagnostic rule is assigned with the same characteristic identifying ID.

The intermediate inference result memory 3 is mainly used to store the intermediate result of inference. If an inferring process relates to reference to the other rules, then the memory is searched in the first place in order to find out whether the rule has been determined. If the rule has already been determined, then the determined result is enabled for direct reference; whereas if the rule has not been determined, the current inferring process is saved and the system turns to inference of the rule being referred to. The saved inferring process will be restored when the inference of the rule being referred to is over. Take the judgment on left ventricular enlargement for example. When there occurs a symptom of left atrial enlargement, the determination of a left ventricle enlargement accordingly has a higher reliability. In the process, it will be first checked whether a left atrial enlargement is determined in an intermediate inference. If it is already determined, then the determined result is referred to directly; whereas if it is not determined yet, the inference of left ventricular enlargement is temporarily saved and the system turns to infer whether there is a left atrial enlargement. When the determination of left atrial enlargement is over, the state of variables and the intermediate results of the inference of left ventricular enlargement are restored, and then the inference of left ventricle enlargement is continued from where they were interrupted. Each time when the inference of one diagnostic rule is over, the result of the inference will be stored into the intermediate inference result memory, whether the result being positive or negative.

The inference machine 4 infers and judges the symbol values of the characteristic parameters based on the diagnostic rules in the diagnostic rule library 5, thereby obtaining a preliminary diagnostic result. Specifically, the inference machine 4 reads diagnostic rules from the symbolized diagnostic rule library 5 in sequence, then judges the symbolized rules and characteristic parameters which are analyzed from the cardiogram signals, thereby obtaining initial diagnostic rules corresponding to the characteristic parameters. If some necessary determination condition is lacked in the inference process, then the current inference process is saved and the lacked determination condition is determined first. The saved inference process is read out and restored when the determination of the lacked condition is over, which is to be continued from where they were suspended. There are cases where some necessary determination conditions are lacked in the inference process, the first one being that some necessary determinations are not conducted due to a sequence for inference. As mentioned above for example, the determination of left ventricle enlargement requires a determination result of left atrial enlargement, whereas the required determination is not conducted yet, then the inference machine suspends the current inference and turns to the required determination of the necessary condition. A second case for lacking necessary determination conditions is that the user fails to input the information needed for the inference process, such as gender, age etc., wherein the system will assign the information with a default value to solve the problem.

Figure 3:
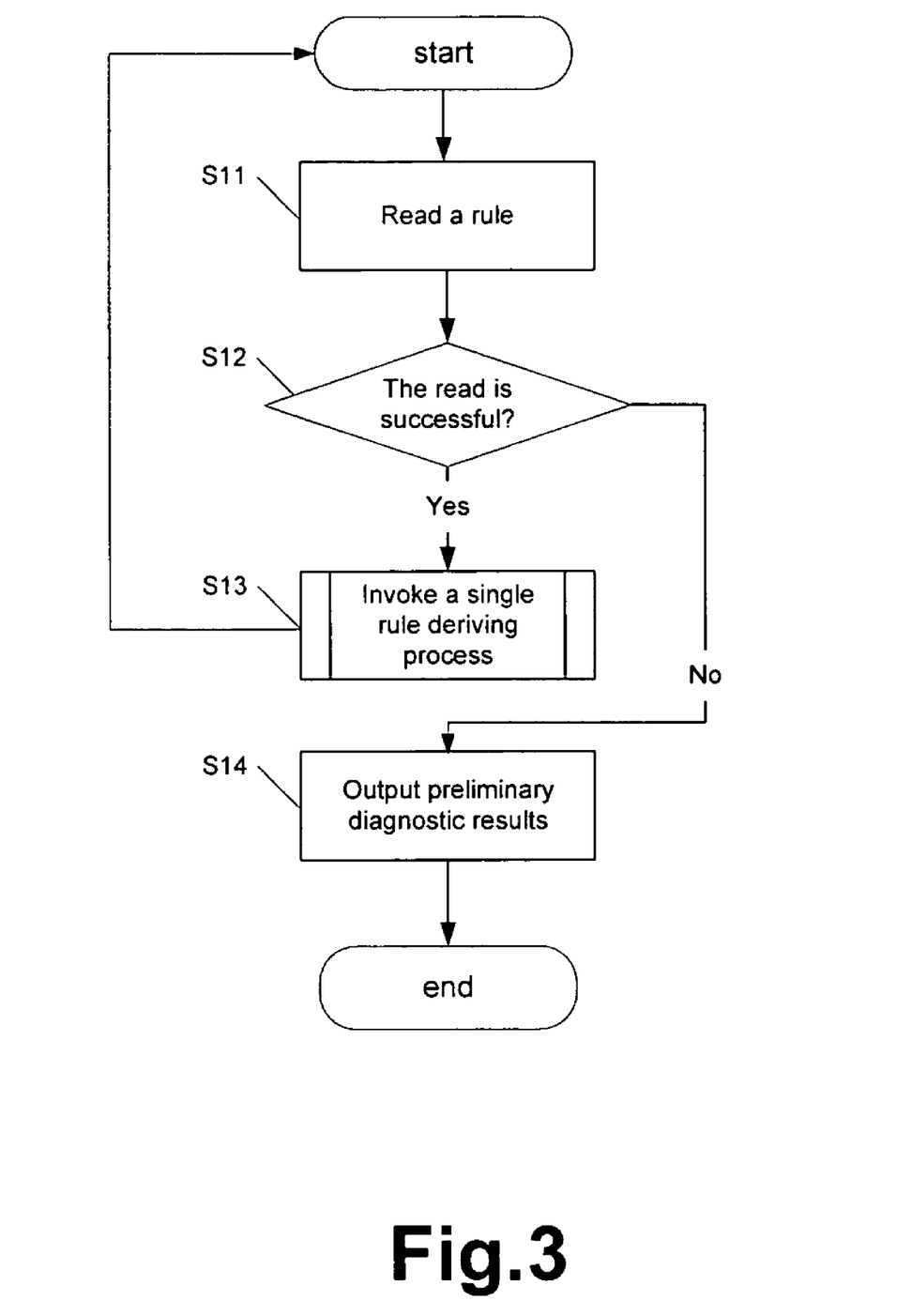
FIG. 3 is a preliminary diagnostic processing flowchart according to one embodiment.

The inference machine 4 serves to determine diagnostic rules, process lacked conditions, record and search the intermediate results. The procedure thereof is shown in the FIG. 3 and FIG. 4, which comprises the following steps:

In step S11, a rule in the diagnostic rule library 5 is read out sequentially, and it proceeds to step S12.

In step S12, it is determined whether the reading process is successful or not: by being successful, it means that there are still unread rules in the diagnostic rule library 5, thereby proceeding to step S13; whereas by being not successful, it means that all the rules in the symbolized diagnostic rules library 5 have been read out, thereby proceeding to S14 for outputting a preliminary diagnostic result.

Figure 4:
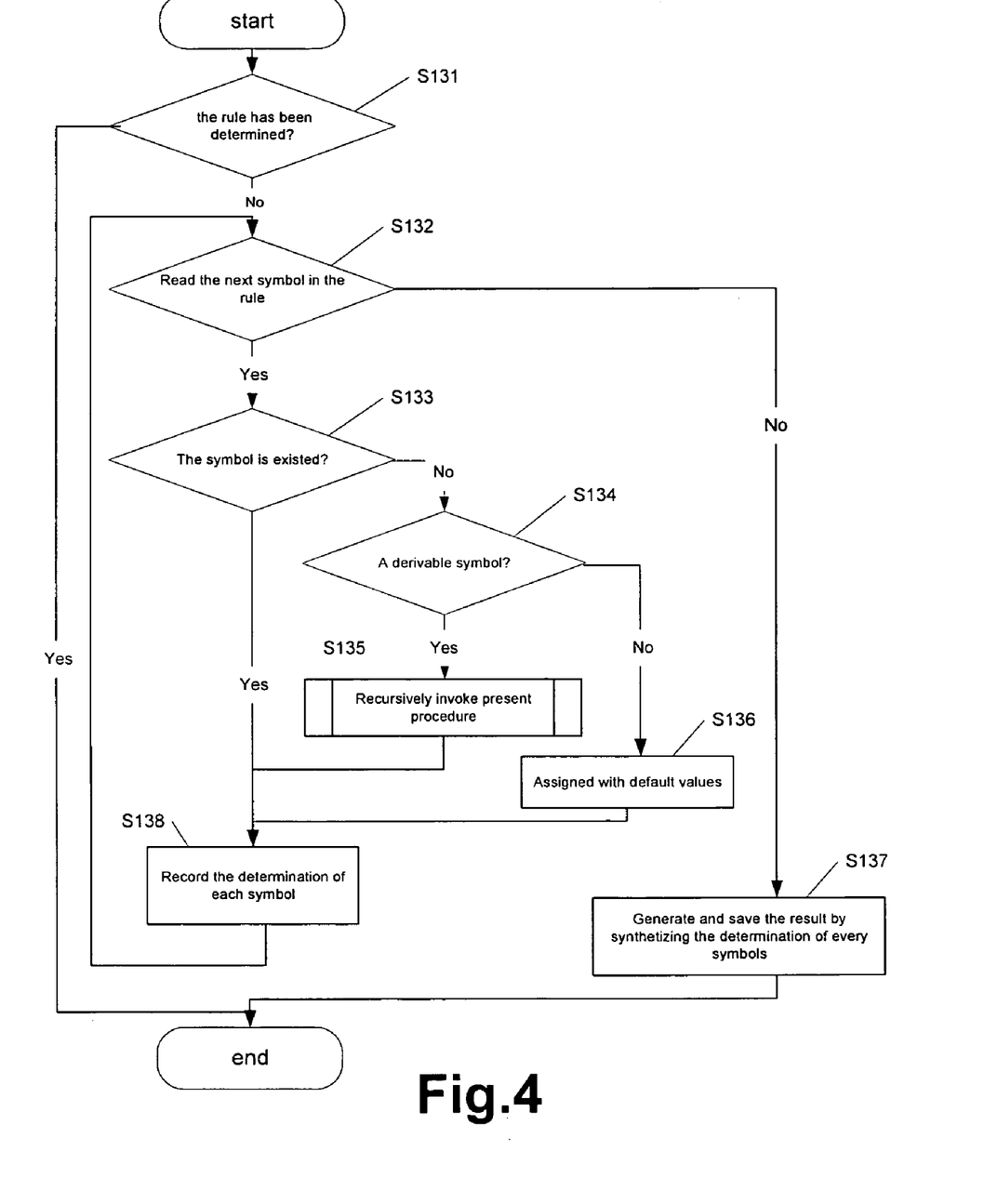
FIG. 4 is a single-rule inference flowchart of a preliminary diagnosis according to one embodiment.

In step S13, a single-rule inference process is invoked, and it turns back to step S11 after the process is invoked, wherein a next diagnostic rule is read out. In the single-rule inference process, it is determined whether each symbol value of the inference rule exists in the symbol values calculated from the characteristic parameters. For those symbol values that do not exist therein, they are assigned with default values or processed with an inference. Specifically, the inference process of a single rule comprises the following steps:

In step S131, it is checked whether the rule has been determined: if the check is positive, the process is closed; otherwise, the process proceeds to step S132.

In step S132, it is determined whether a next symbol in the rule is going to be read: if it is, the process goes to step S133; otherwise, it goes to step S137; wherein a result of the diagnostic rule inference is generated and saved by synthesizing the determined results of the respective symbols.

In step S133, it is determined whether the symbol value exists or not: if it exists, the process goes to S138; otherwise, it means lack of a necessary condition and the process goes to step S134.

In step S134, it is determined whether the symbol is inferable: if yes, the process goes to step S135 for recursively invoking the current single-rule inference process; otherwise, the process goes to step S136, wherein the symbol is assigned with a default value. Then, the process goes on to step S138.

In step S138, a result of the symbol determination is recorded and the process goes to step S132.

The derived preliminary diagnostic result comprises one result or several results. Each preliminary diagnostic result is assigned with a same characteristic identifying ID as that of the corresponding rule in the diagnostic rule library 5.

The conflict eliminating rule library 9 is used to store the discriminating relations and priority levels of the diagnostic types which can be confused easily. The conflict eliminating device 8 is used to discriminate and analyze those preliminary diagnostic results based on the content of the conflict eliminating rule library, in order to optimize the preliminary diagnostic results. Initially, the library is furnished with definitions from the relating literatures, while it can be subsequently improved according to the differences between human and program-based judgments.

Figure 5:
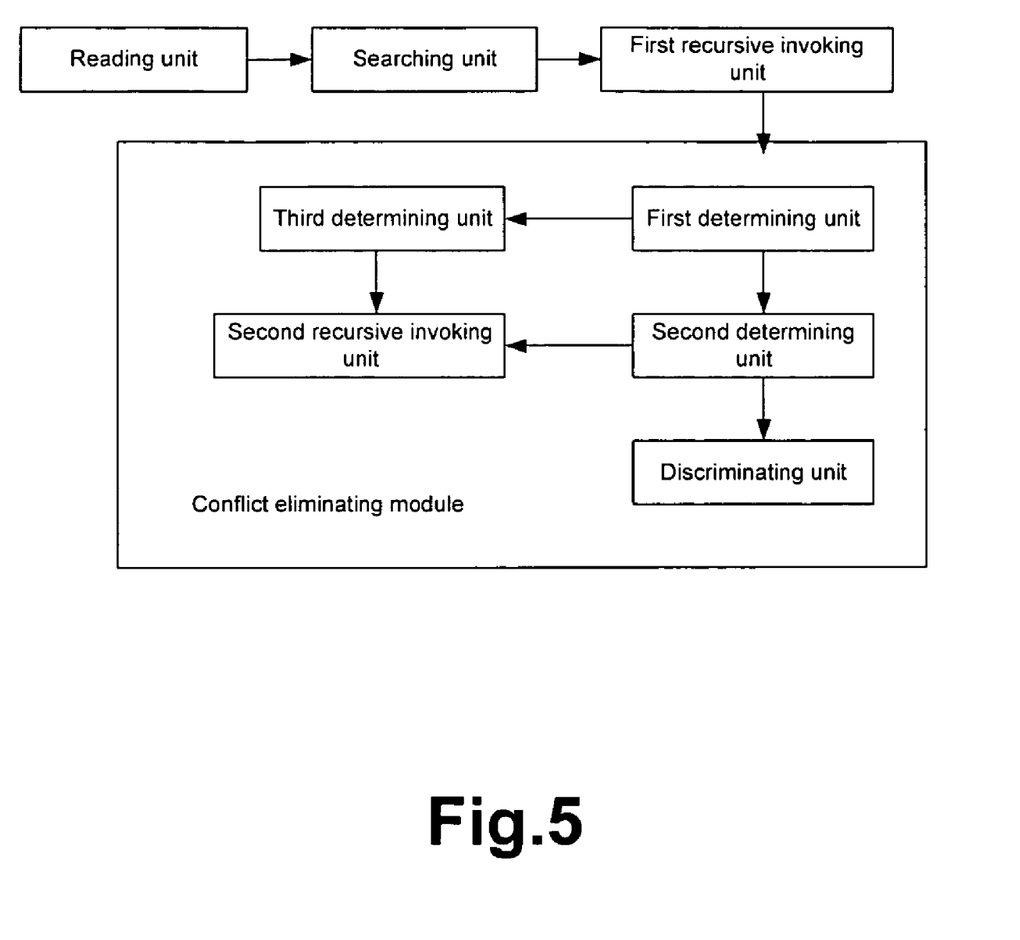
FIG. 5 is a block diagram showing a conflict eliminating circuit connection according to one embodiment.

The conflict eliminating device 8 is used to discriminate and analyze each preliminary diagnostic result. Since there are many types of diagnostic pathology and the definitions in the conflict eliminating rule library 5 are converted from the clinical experience of the physicians directly, the descriptions of the cardiogram signals may likely be incomplete. Accordingly, the discrimination of similar cases must be distinguished form each other by some particular details, or by optimizing some particular diagnostic results for a final optimized result. The conflict eliminating device accomplishes the detail-based discrimination and mutex processing between those preliminary diagnostic results based on the conflict eliminating rule library 9. A circuit thereof is shown in FIG. 5, which comprises: a reading unit, a searching unit, a first recursive invoking unit and a conflict eliminating module, wherein, the conflict eliminating module includes a first determining unit, a second determining unit, a third determining unit and a second recursive invoking unit. The reading unit is used to read the characteristic identifying ID in the preliminary diagnostic result list sequentially, and to treat the characteristic identifying ID as a currently to-be-discriminated ID. The searching unit is used to search in the conflict eliminating rule library for a node with the type ID that is identical with the currently to-be-discriminated ID, wherein the searching is conducted by taking left child node in the first place; and a control signal is output to the reading unit when the node is not found, while a control signal is output to the first recursive invoking unit when the node is found. The first recursive invoking unit is used to receive the control signal output, by the searching unit, and to recursively invoke a conflict eliminating module. The first determining unit is used to determine whether the type ID of current node is included in the preliminary diagnostic result, wherein a control signal is output to the second determining unit when the determination is positive, and a control signal is output to a third unit determining unit when the determination is negative. The second determining unit is used to determine whether the current node has a left child node in response to the control signal output by the first determine unit, wherein a control signal is output to a second recursive invoking unit when the determination is positive and a control signal is output to a discriminating unit when the determination is negative. The second recursive invoking unit is used to recursively invoke the conflict eliminating module. The discriminating unit is used to make a discrimination by invoking the discrimination function of the current node, and thus to delete the type that should be removed from the preliminary diagnostic result list based on the result of the discrimination. The third determining unit is used to determine whether the current node has a right child node, and output a control signal to the second recursive invoking unit when the determination is positive.

Figure 6:
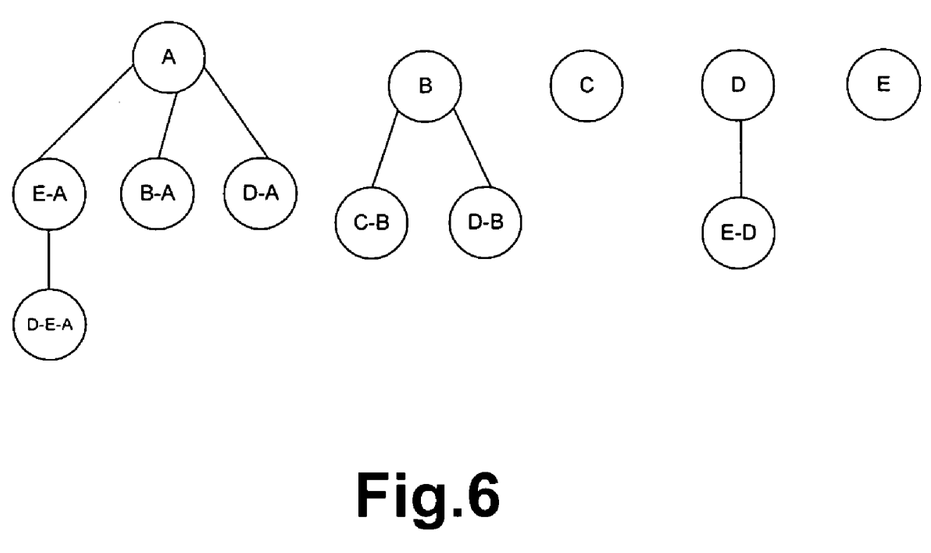
FIG. 6 is a diagram displaying the discriminating relations between types according to a clinical comparison result.

The symbolized diagnostic rule library 5 contains some basic rules that carry many loopholes when being applied to actual signal judgments. Therefore, clinical tests of signals in practice there based often produce misjudgments. A tree structure is adopted therefore to store the method for eliminating those conflicts in order to simplify the optimizing process. It is assumed that a number of misjudgments are resulted from a series of clinical data tests between some diagnostic types, such as A, D and E; A and B; D and A; B and C; B and D; E and D (e.g. misjudgment leading to a confusion between the diagnoses, or misjudgment leading to the conclusion of co-existence of several different diagnoses). Then corresponding conflict trees can be constructed, as shown in FIG. 6. The trees without child nodes in the figure do not need discriminating diagnoses, while those structures are reserved in order to facilitate an improvement in the future. The multi-branch tree is then converted into a binary tree, in which all the child nodes are converted into a left child tree, and all the sibling nodes are converted into a right child tree, as shown in the FIG. 7. It should be noted that, if a "right child node first" principle is adopted, then all the child nodes should be converted into a right child tree, and all the sibling nodes should be converted into a left child tree.

Figure 7:
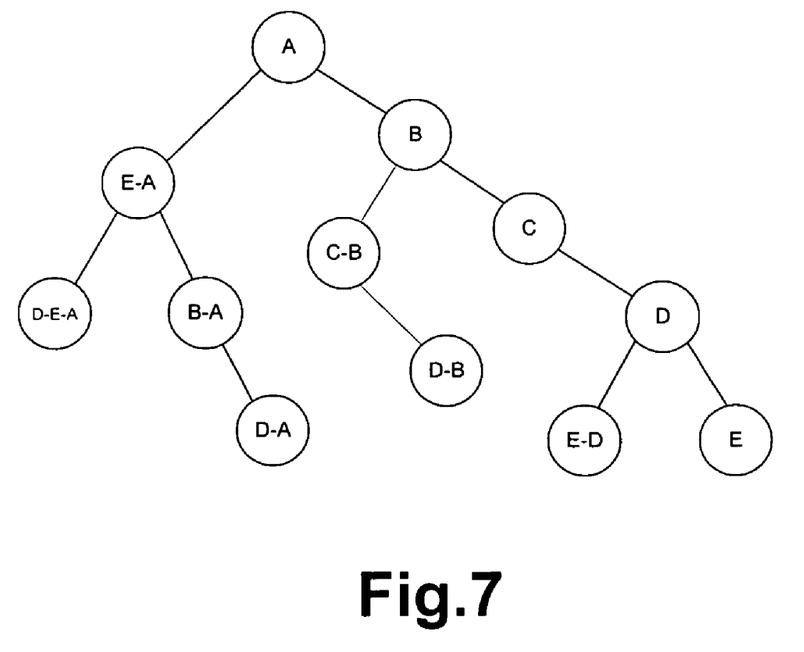
FIG. 7 is a diagram showing the conflict eliminating tree used in the actual inferences.

The nodes for discrimination between X, Y, Z types is denoted as X-Y-Z in the figure. The corresponding type ID, discrimination function, pointers to left and right child nodes are included in each child node. For example, node B-A has a characteristic identifying ID whose type ID is B. A discrimination function is used to determine the type sequence formed to the left child tree. That is, the discrimination function in each left child node of the conflict eliminating tree is used to discriminate between the node and its parent node. For example, the discrimination function in node E-A is used to discriminate between type E and type A; the discrimination function in node D-E-A is used to discriminate between type D, type E and type A; and discrimination function in node B-A is used to discriminate between type B and type A. The pointers to left and right child nodes are directed to the left child node and the right child node of said node respectively.

As shown in FIG. 7, the discrimination therein can include either a process for distinguishing and judging two types through some details, or a preferred/mutex (an optimum seeking or mutually excluding) process between different types. The preferred (optimum seeking) process can be performed in such a manner that if it is a parent node and a child node that are to be discriminated, the final discrimination result is the parent node. For example, the judgment of a signal shows that there are two types of diagnoses, namely, left atrial enlargement and bi-atrial enlargement. It is obvious that the bi-atrial enlargement covers the left atrial enlargement. Thus such a conflict tree can be adopted as the parent node being bi-atrial enlargement and the left child node being left atrial enlargement. Accordingly, the result of the discrimination is bi-atrial enlargement. If a mutex (mutually excluding) process is adopted, the priority levels of respective types are used for making the above judgment. For example, the priority level of bi-atrial enlargement is defined higher than that of left atrial enlargement. Therefore, the bi-atrial enlargement is returned as the final result of the discrimination.

Figure 8:
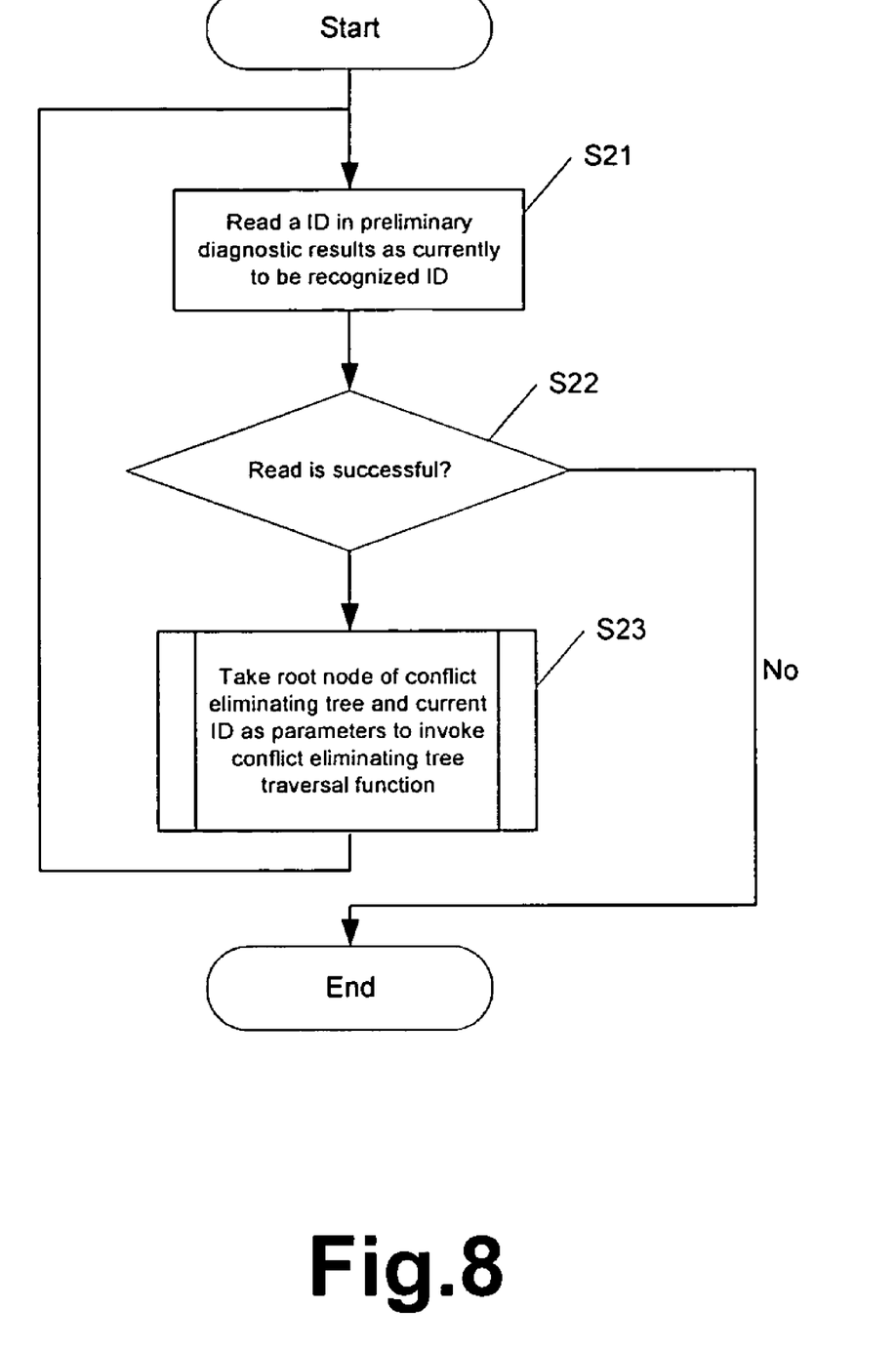
FIG. 8 is a main flowchart of conflict elimination according to one embodiment.
Figure 9:
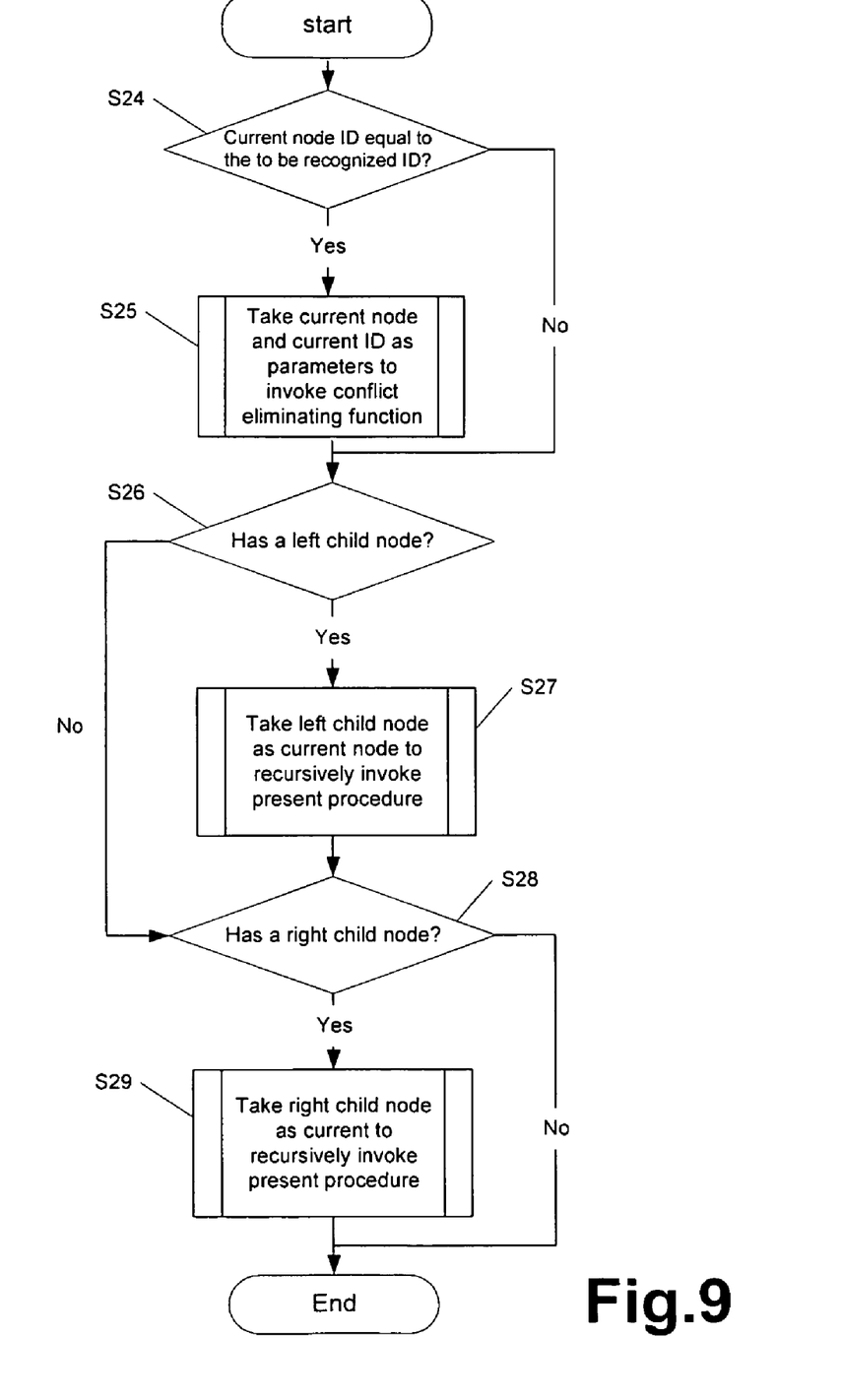
FIG. 9 is a flowchart of the conflict-eliminating traversal function according to one embodiment.
Figure 10:
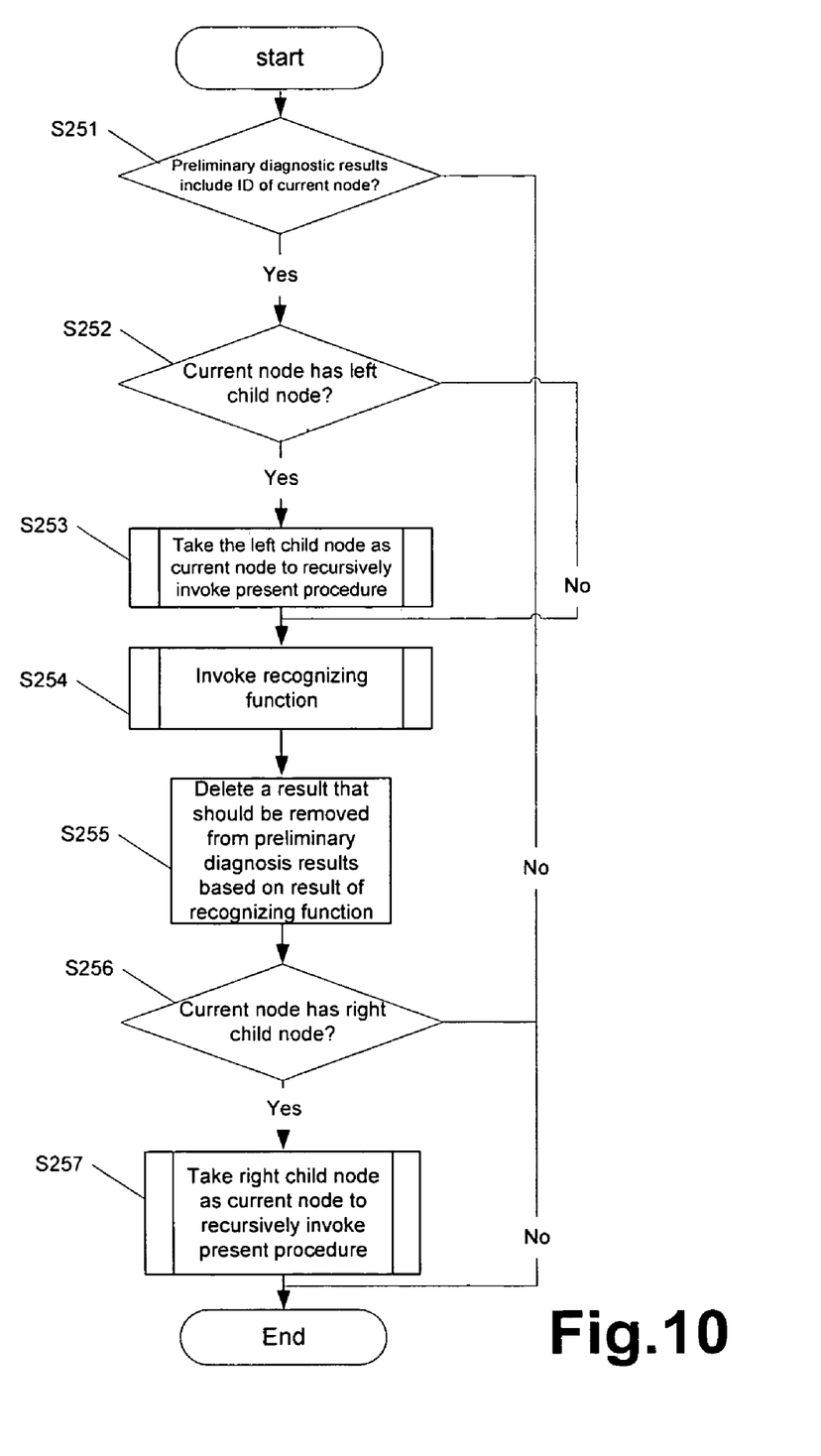
FIG. 10 is a flowchart of the conflict eliminating process according to one embodiment.

The conflict eliminating process is shown in FIGS. 8-10, which comprises the following steps:

In step S21, a next characteristic identifying ID is read from the preliminary diagnostic result list sequentially, and it is treated as a currently to-be-discriminated ID, then the process goes to step S22.

In step S22, it is determined that whether the reading process is successful or not. If successful, it means that there are still unread diagnostic rules in the preliminary diagnostic result list, then the process proceeds to step S23; if not successful, it means that there are no undiscriminated diagnostic result in the preliminary diagnostic result list, then the discrimination process is over, and the final diagnostic result is outputted.

In step S23, the root node of the conflict eliminating tree and the currently to-be-discriminated ID are taken as parameters for invoking the conflict eliminating tree traversal function, and the process turns to step S21 after each invoking, in order to discriminate a next preliminary diagnostic result.

The process flow of the conflict eliminating tree traversal function is shown in FIG. 9, which comprises the following steps:

In step S24, the root node of the conflict eliminating tree and the currently to-be-discriminated ID are taken as parameters for determining whether the type ID of the current node in the conflict eliminating tree is the same as the currently to-be-discriminated ID. If they are the same, the process goes to step S25, otherwise, it goes to step S26.

In step S25, the current node and the currently to-be-discriminated ID are taken as parameters, for eliminating those existing conflicts by invoking the conflict eliminating function. The conflict eliminating function will be described later in detail. The process goes to step S26 after the conflict eliminating function is invoked.

In step S26, it is determined whether the current node has a left child node based on the pointers of left and right child nodes of the current node. If there is a left child node, the process goes to step S27; if not, it goes to step. S28.

In step S27, it takes the left child node as the current node, and recursively invokes the conflict eliminating tree traversal function. Then the process goes to step S28.

In step S28, it is determined whether the current node has a right child node. If there is a right child node, the process goes to step S29; if not, the process is over.

In step S29, it takes the right child node as the current node, and recursively invokes the conflict eliminating tree traversal function. Then the process is over.

The process flow of the conflict eliminating function is described hereunder in reference to FIG. 10, which comprises the following steps:

In step S251, it is determined whether the preliminary diagnostic result has the type ID of the current node. If the result has such a type ID, the process goes to step S252, and if not, the process is over.

In step S252, it is determined whether the current node has a left child node. If yes, the process goes to step S253; if no, the process goes to step S254.

In step S253, it takes the left child node as the current node, and recursively invokes the conflict eliminating function. Then the process goes to step S254.

In step S254, it invokes the discrimination function of the current node and makes discrimination. Then the process goes to step S255, wherein the type that should be removed from the preliminary diagnostic result list is deleted according to the result returned by the discrimination function. Then the process goes to step S256.

In step S256, it is determined whether the current node has a right child node. If there is a right child node, the process goes to step S257, if not, the process is over.

In the step S257, it takes the right child node as the current node, and recursively invokes the conflict eliminating function.

In summary, the present application features a simple system structure, and requires only a small number of system resources. It can be applied to small systems, such as a single-chip system. Such two processes as the preliminary judgment and the conflict elimination adopted therein are similar to those of human judgment and discrimination, and the optimization of the system is also similar to a human learning procedure. In the preliminary judging process, all the possible diagnostic results are determined on the basis of the characteristics of cardiogram. Therefore, the structure of the system is simplified. The discrimination process comprises a further analysis and judgment on the details of the preliminary results, by which the accuracy of the system is enhanced. Since the preliminary judging process and the conflict eliminating process are adopted in the system, the system update can be thus limited to a smaller scope of the system. Since the preliminary diagnosis produces basically correct outcomes, the conflict elimination process is mainly directed to compensating for the parts missed in the preliminary diagnosis, and such compensation can be completed by adding new sub-trees into the initial tree structure without largely modifying the whole system. In developing the system, human check procedure may be provided for checking a difference between the final result outputted by the system and the human judgment, according to which the physician diagnostic rule library and the conflict eliminating procedure are constantly amended and improved so that the output result of the system can be made increasingly close to the judgment of physician by modifying the over and over.

The advantages are:

(1) The embodiment separates the diagnostic procedure into two phases, that is, a preliminary judging process and a conflict eliminating procedure. In the preliminary judging process, the characteristic parameters of the cardiogram are symbolized and are inferred according to the diagnostic rules in the diagnostic rules library. A series of preliminary diagnostic results are obtained form the process. In the conflict eliminating procedure, a conflict eliminating structure is constructed by binary tree structure for the result of foregoing process. A reliable conclusion is drawn from the discrimination process and the comparison between different priority levels.

(2) The embodiment confines the complex judgment into some phase of the system, and therefore the whole inference procedure, by which a lot of pathological signals can be determined, is simple and accurate. When the system needs modification, the diagnostic rules can be added by adding child nodes into the conflict eliminating tree structure. Therefore, the system can be optimized without modifying original parts, and it can be maintained, updated and improved without any difficulty.

(3) An intermediate inference result storing unit is provided in the system, and therefore, the calculating efficiency thereof is improved.

The preferable embodiments are described for the purpose of illustration, and it is not intended to exhaust all the possible embodiments or limit the invention into those disclosed embodiments. It can be appreciated by those skilled in the art that all the modifications and changes are apparent.

The invention claimed is:

1. A cardiogram diagnostic system, comprising:
   a diagnostic module, for obtaining a plurality of preliminary diagnostic results according to received cardiogram signals;
   a conflict eliminating module comprising a conflict eliminating rule library including conflict eliminating rules, the conflict eliminating module for automatically judging the plurality of preliminary diagnostic results, and automatically amending the plurality of preliminary diagnostic results using the conflict eliminating rules, in order to obtain amended diagnostic results;
   a diagnostic rule library, for storing various rules of diagnosis of pathological signals relating to the received cardiogram signals, wherein each diagnostic rule in the diagnostic rule library is assigned with a corresponding characteristic identifying ID;
   wherein the conflict eliminating module further comprises:
   a reading unit, for reading the characteristic identifying ID and treating the read characteristic identifying ID as a currently to-be-discriminated ID; and
   a searching unit, for searching in the conflict eliminating rule library for a child node in a binary tree structure with a type ID that is the same as the currently to-be-discriminated ID, wherein the search is conducted in such a manner that the child node in one side of the binary tree structure is taken in the first place; thereby outputting a read signal when the child node is not found and outputting a first recursive invoking signal when the child node is found, wherein the read signal triggers the reading unit to read a next characteristic identifying ID; and
   an output module, for outputting the amended diagnostic results.

2. The cardiogram diagnostic system of claim 1, wherein the conflict eliminating rule library further stores discriminating relations and priority levels of different types of preliminary diagnostic results, the discriminating relations being used for discriminating between the preliminary diagnostic results based on the conflict eliminating rules; and
   wherein the conflict eliminating module further comprises
   a conflict eliminating device, for analyzing the preliminary diagnostic results based on the discriminating relations and priority levels stored in the conflict eliminating rule library, and obtaining the amended diagnostic results by processing the preliminary diagnostic results.

3. The cardiogram diagnostic system of claim 2, wherein the conflict eliminating device deletes types that should be removed from the preliminary diagnostic results by use of the discriminating relations in order obtain the amended diagnostic results.

4. The cardiogram diagnostic system of claim 2, wherein the conflict eliminating device deletes types that should be removed from the preliminary diagnostic results based on the priority levels in order to obtain the amended diagnostic results.

5. The cardiogram diagnostic system of claim 2, wherein the discriminating relations are associated with respective nodes arranged in the binary tree structure in the conflict eliminating rule library, the binary tree structure defining the conflict eliminating rules between the different types of preliminary diagnostic results.

6. The cardiogram diagnostic system of claim 1, wherein the diagnostic module comprises:
   a symbol set, for storing symbols abstracted from parameters used in cardiogram diagnoses;
   a characteristic parameter calculating and symbolizing device, for receiving cardiogram signals, calculating the characteristic parameters of the cardiogram signals, and determining symbol values of the characteristic parameters according to the symbol values defined for the cardiogram diagnostic parameters in the symbol set;
   wherein the diagnostic rule library converts each diagnostic rule into symbols according to the symbols defined for cardiogram diagnostic parameters in the symbol set;
   an inferring device, for inferring the symbol values of the characteristic parameters calculated from the cardiogram signals based on the diagnostic rules in the diagnostic rule library, and determining the preliminary diagnostic results; and
   wherein the preliminary diagnostic result determined from the diagnostic rule is assigned with the same characteristic identifying ID.

7. The cardiogram diagnostic system of claim 6, further comprising:
   a memory, for storing intermediate inference results of the inferring device;

wherein, if the inference process involves reference to the other rules, then the conflict eliminating unit searches the stored intermediate inference results in the first place, in order to find out whether the rule has been determined or not; if the rule has already been determined, the determined rule is enabled for direct reference; whereas if the rule has yet to be determined, then the current inference process is saved and the system turns to inference of the rule being referred to, wherein the saved inference process is restored after the inference of the rule being referred to is over.

8. The cardiogram diagnostic system of claim 6, wherein the conflict eliminating module further comprises:
   a first recursive invoking unit, for recursively invoking, in response to the first recursive invoking signal:
      a first determining unit, for determining whether the type ID of a current node is included in the preliminary diagnostic results, outputting a second determining unit signal when the type ID of current node is included in the preliminary diagnostic results, and outputting a third determining unit signal when the type ID of current node is not included in the preliminary diagnostic results;
      a second determining unit, for determining whether the current node has a child node in said side in response to the second determining unit signal, outputting a second recursive invoking signal when the current node has a child node in said side, and outputting a discrimination processing signal when the current node does not have a child node in said side;
      a second recursive invoking unit, for recursively invoking the conflict eliminating module in response to the second recursive invoking signal;
      a discriminating unit, for making discrimination in response to the discrimination processing signal, and deleting the type that should be removed from the preliminary diagnostic results based on a result of the discrimination; and
      a third determining unit, for determining whether the current node has a child node in the other side in response to the third determining unit signal, and outputting the second recursive invoking signal to the second recursive invoking unit when the current node has a child node in the other side.

9. A computer assisted cardiogram diagnostic method, comprising:
   a diagnosing step, for obtaining a plurality of preliminary diagnostic results according to received cardiogram signals;
   a conflict eliminating step, for automatically judging the plurality of preliminary diagnostic results, and automatically amending the plurality of preliminary diagnostic results by use of conflict eliminating rules in a conflict eliminating rule library without user intervention, in order to obtain amended diagnostic results;
   a diagnostic rule storing step, for storing various diagnostic rules of pathological signals relating to the received cardiogram signals, wherein each diagnostic rule in the diagnostic rule storing step is assigned with a corresponding characteristic identifying ID;
   wherein the conflict eliminating step further comprises:
      a reading step, for reading the characteristic identifying ID and treating the read characteristic identifying ID as a currently to-be-discriminated ID; and
      a searching step, for searching a child node in a binary tree structure with a type ID that is the same as the currently to-be-discriminated ID, wherein the search is conducted in such a manner that the child node in one side of the binary tree structure is taken in the first place; thereby going to reading step when the node is not found and going to first recursive invoking step when the node is found; and
   an output step, for outputting the amended diagnostic results on an output device.

10. The computer assisted cardiogram diagnostic method of claim 9, wherein the conflict eliminating step comprises:
   storing discriminating relations and priority levels of different types of preliminary diagnostic results, the discriminating relations being used for discriminating between the preliminary diagnostic results based on the conflict eliminating rules; and
   analyzing the preliminary diagnostic results based on the stored discriminating relations and priority levels, and obtaining the amended diagnostic results by processing the preliminary diagnostic results.

11. The computer assisted cardiogram diagnostic method of claim 9, wherein the conflict eliminating step deletes types that should be removed from the preliminary diagnostic results by use of the discriminating relations in order obtain the amended diagnostic results.

12. The computer assisted cardiogram diagnostic method of claim 9, wherein the conflict eliminating step deletes types that should be removed from the preliminary diagnostic results by use of the priority levels in order to obtain the amended diagnostic results.

13. The computer assisted cardiogram diagnostic method of claim 10, wherein the binary tree structure is adopted in the conflict eliminating step to define the conflict eliminating rules between the different types of preliminary diagnostic results.

14. The computer assisted cardiogram diagnostic method of claim 9, wherein the diagnosing step comprises:
   a symbol storing step, for storing symbols abstracted from parameters used in cardiogram diagnoses;
   a characteristic parameter calculating and symbolizing step, for receiving cardiogram signals, calculating the characteristic parameters of the cardiogram signals, and determining symbol values of the characteristic parameters according to the symbol values defined for the cardiogram diagnostic parameters in the symbol storing step;
   wherein the diagnostic rule storing step converts each diagnostic rule into symbols according to the symbols defined for cardiogram diagnostic parameters in the symbol storing step; and
   an inferring step, for inferring the symbol values of the characteristic parameters based on the diagnostic rules in the diagnostic storing step, and determining the preliminary diagnostic results;
   wherein the preliminary diagnostic result determined from the diagnostic rule is assigned with the same characteristic identifying ID.

15. The computer assisted cardiogram diagnostic method of claim 14, further comprising a storing step, for storing intermediate inference results of the inferring step;
   wherein, if the inferring step involves reference to the other rules, then searching the stored intermediate deriving results in the first place, in order to find out whether the rule has been determined or not; if the rule has already been determined, the determined rule is enabled for direct reference; whereas if the rule has yet to be determined, then the current inference process is saved and turns to inference of the rule being referred to, wherein the saved deriving process is restored after the inference of the rule being referred to is over.

16. The computer assisted cardiogram diagnostic method of claim 14, wherein the conflict eliminating step further comprises:
   a first recursive invoking step, for recursively invoking the steps of:
      a first determining step, for determining whether the type ID of current node is included in the preliminary diagnostic results, going to a second determining step when the type ID of a current node is included in the preliminary diagnostic results, and going to a third determining step when the type ID of the current node is not included in the preliminary diagnostic results;
      a second determining step, for determining whether the current node has a child node in said side, going to a second recursive invoking step when the current node has a child node in said side, and going to a discriminating step when the current node does not have a child node in said side;
   a second recursive invoking step, for recursively invoking the conflict eliminating step;
   a discriminating step, for making discrimination and deleting the type that should be removed from the preliminary diagnostic results based on a result of the discrimination; and
   a third determining step, for determining whether the current node has a child node in the other side, and going to a second recursive invoking step when the current node has a child node in the other side.

* * * * *